US008318713B2

(12) United States Patent
Chedid et al.

(10) Patent No.: US 8,318,713 B2
(45) Date of Patent: Nov. 27, 2012

(54) POTENTIATION OF CANCER CHEMOTHERAPY BY 7-(2, 5-DIHYDRO-4-IMIDAZO [1, 2-A] PYRIDINE-3-YL-2,5-DIOXO-1H-PYRROL-3-YL)-9-FLUORO-1,2,3,4 TETRAHYDRO-2-(1-PIPERIDINYL-CARBONYL)-PYRROLO [3,2,1-JK] [1,4] BENZODIAZEPINE

(75) Inventors: Marcio Chedid, Fishers, IN (US); Thomas Albert Engler, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 384 days.

(21) Appl. No.: 12/664,664

(22) PCT Filed: Jun. 20, 2008

(86) PCT No.: PCT/US2008/067614
§ 371 (c)(1),
(2), (4) Date: Dec. 15, 2009

(87) PCT Pub. No.: WO2009/006043
PCT Pub. Date: Jan. 8, 2009

(65) Prior Publication Data
US 2010/0166884 A1 Jul. 1, 2010

Related U.S. Application Data

(60) Provisional application No. 60/947,512, filed on Jul. 2, 2007.

(51) Int. Cl.
*A01N 43/00* (2006.01)
*A01N 43/62* (2006.01)
*A61K 31/33* (2006.01)
*A61K 31/55* (2006.01)

(52) U.S. Cl. ..................... 514/183; 514/220
(58) Field of Classification Search .......... 514/183, 514/220
See application file for complete search history.

(56) References Cited

U.S. PATENT DOCUMENTS

| | | | |
|---|---|---|---|
| 5,134,127 A | 7/1992 | Stella et al. |
| 5,376,645 A | 12/1994 | Stella et al. |
| 5,721,245 A | 2/1998 | Davis et al. |
| 7,491,716 B2 | 2/2009 | Engler |
| 2004/0097517 A1 | 5/2004 | Dwyer et al. |

FOREIGN PATENT DOCUMENTS

| | | |
|---|---|---|
| WO | WO 03/076442 | 9/2003 |
| WO | WO 03/080079 A1 | 10/2003 |
| WO | WO 2006/006939 | 1/2006 |
| WO | WO 2006/018633 | 2/2006 |

OTHER PUBLICATIONS

Vippagunta et al. Advanced Drug Delivery Reviews, 2001, vol. 48, pp. 3-26.*
Hanna et al. Journal of Clinical Oncology, 2004, vol. 22, No. 9, pp. 1589-1597.*
Azzoli et al. Journal of National Cancer Institute, Jun. 6, 2007, vol. 99, Issue 11, pp. 828-829.*
Cao, Q. et al, "Glycogen synthase kinase-3 beta positively regulates the proliferation of human ovarian cancer cells", Cell Research (2006) 16:671-677.
Panka, D. et al, "GSK-3 beta Inhibition Enhances Sorafenib-induced Apoptosis in Melanoma Cell Lines", The Journal of Biological Chemistry (2008) 283(2):726-732.
Van Wauwe, J., Haefner, B., "Glycogen Synthase Kinase-3 as Drug Target: From Wallflower to Center of Attention", Drug News Perspect (2003) 16(9):557-565.
Kulkarni, N., et al., "Changes in Osteoblast, Chondrocyte, and Adipocyte Lineages Mediate the Bone Anabolic Actions of PTH and Small Molecule GSK-3 Inhibitor," Journal of Cellular Biochemistry, vol. 102, pp. 1504-1518 (2007).
Kulkarni, N., et al., "Orally Bioavailable GSK-3alpha/beta Dual Inhibitor Increases Markers of Cellular differentiation in Vitro and Bone Mass in Vivo," Journal of Bone and Mineral Research, vol. 21, No. 6, pp. 910-920 (2006).
Dong et al., "Role of glycogen synthase kinase 3B in rapamycin-mediated cell cycle regulation and chemosensitivity," Cancer Research, 65(5):1961-1972 (2005).
Engler, et al., "Substituted 3-Imidazo[1,2-a]pyridine-3-yl-4-(1,2,3,4-tetrahydro-[1,4]diazepino-[6,7,1-hi]indol-7-yl) pyrrole-2,5-diones as highly selective and potent inhibitors of glycogen synthase kinase-3," Journal of Medicinal Chemistry, 47:3934-3937 (2004).
Engler, et al., "The development of potent and selective bisarylmaleimide GSK3 inhibitors," Bioorganic & Medicinal Chemistry Letters, 15:899-903 (2005).
Liao, et al., "Glycogen synthase kinase-3B suppression eliminates tumor necrosis factor-related apoptosis-inducing ligand resistance in prostate cancer," Molecular Cancer Therapeutics, 2:1215-1222 (2003).

(Continued)

*Primary Examiner* — Samira Jean-Louis
(74) *Attorney, Agent, or Firm* — John C. Demeter; Robert Titus

(57) ABSTRACT

A method for treating gastric cancer, ovarian cancer, non-small cell lung cancer, or colorectal cancer in a patient is described, as well as pharmaceutical compositions comprising 7-(2,5-dihydro-4-imidazo[1,2-a]pyridine-3-yl-2,5-di-oxo-IH-pyrrol-3-yl)-9-fluoro-1,2,3,4-tetrahydro-2-(1-piperidinyl-carbonyl)-pyrrolo[3,2,1-jk][1,4]benzodiazepine, useful for the method and a process for preparing said compositions.

5 Claims, No Drawings

OTHER PUBLICATIONS

Liu, "Targeting GSK3B as an effective approach to modulate chemotherapy-induced apoptosis in colon cancer cells," Eli Lilly and Company, Lilly Corporate Center, Indianapolis, Indiana, Nov./Dec. 2004.

Schoette, et al., "Lithium sensitizes tumor cells in an FK-kB-independent way to caspase activation and apoptosis induced by tumor necrosis factor (TNF)," The Journal of Biological Chemistry, 276(28):25939-25945 (2001).

Tan, et al., "Pharmacologic modulation of glycogen synthase kinase-3B promotes p53-dependent apoptosis through a direct Bax-medicated mitochondrial pathway in colorectal cancer cells," Cancer Res., 65(19):9012-9020 (2005).

Rottmann, Sabine, et al., "A Trail receptor-dependent synthetic lethal relationship between MYC activation and GSK3β/FBW7 loss of function," Proceedings of the National Academy of Sciences 102(42):15195-5200 (2005).

Ed. Rowe, Raymond C., Handbook of Pharmaceutical Excipients, 5th ed. London: Pharmaceutical Press, 754-57; 770-71 (2006).

* cited by examiner

POTENTIATION OF CANCER CHEMOTHERAPY BY 7-(2, 5-DIHYDRO-4-IMIDAZO [1, 2-A] PYRIDINE-3-YL-2,5-DIOXO-1H-PYRROL-3-YL)-9-FLUORO-1,2,3,4 TETRAHYDRO-2-(1-PIPERIDINYL-CARBONYL)-PYRROLO [3,2,1-JK] [1,4] BENZODIAZEPINE

This application is a national phase application under 35 U.S.C. Section 371 of PCT/US2008/067614, filed Jun. 20, 2008, which claims the benefit under 35 U.S.C. Section 119 of U.S. provisional patent application 60/947,512, filed Jul. 2, 2007.

BACKGROUND OF THE INVENTION

The efficacy of any cancer chemotherapy is limited by the sensitivity of specific cancers to a particular treatment. Even when a cancer is responsive to a particular chemotherapy, acute and chronic toxic effects associated with the chemotherapy often force a reduction in dose or discontinuation of treatment altogether. One approach to treatment of non-responsive cancers or to overcome dose-limiting toxicity is to combine agents which act via different mechanisms of action. Although some advantageous chemotherapy combinations have been discovered, the identification of combinations of agents that demonstrate improved efficacy at a particular cancer or that are better tolerated by the patient remains essentially empirical.

Glycogen synthase kinase 3β (GSK3β) is a serine/threonine kinase implicated in various signal transduction networks known to regulate a variety of cell functions. The role of GSK3β in cancer treatment is unclear. Rapamycin, for example, is reported to dramatically potentiate the effects of paclitaxel, vinorelbine, and carboplatin, but not the effects of doxorubicin or gemcitabine, in breast cancer cells by activation of GSK3β. This potentiation was inhibited by the well-known GSK3β inhibitors lithium chloride, SB216763, and SB415286. (Dong, et al., *Cancer Research*, 65(5), 1961-1972 (2005)) In contrast, lithium chloride and SB216763, inhibitors of GSK3β, have been shown to dramatically potentiate the anti-tumor efficacy of tumor necrosis factor-related apoptosis-inducing ligand (TRAIL) in both p53 positive and p53 negative prostate cancer cells at sub-toxic concentrations. (Liao, et al., *Molecular Cancer Therapeutics*, 2, 1215-1222 (2003)) Similarly, lithium chloride was shown to sensitize tumor cells to tumor necrosis factor (TNF) in human rhabdomyosarcoma cells and murine fibrosarcoma cells, but GSK3β inhibitors Ro31-8220, valproic acid, and indirubin-3'-monoxime failed to potentiate the same effect. (Schoette, et al., *The Journal of Biological Chemistry*, 276(28), 25939-25945 (2001)) Finally, GSK3β inhibitors lithium chloride and LY2119301 are reported to potentiate the effects of adriamycin, etoposide, and 5-fluorouracil in p53 positive colon cancer cells, but neither SB216763 nor SB415286 potentiated the effects of any agent tested, and all of the GSK3β inhibitors tested failed to demonstrate the desired potentiation in p53 negative colon cell lines. (Tan, et al., *Cancer Research*, 65(19), 9012-9020 (2005)).

There is a need for specific combinations of agents that exhibit improved efficacy in the treatment of a cancer patient with a particular cancer, or that allows a cancer patient to better tolerate chemotherapy. The GSK3β inhibitor 7-(2,5-dihydro-4-imidazo[1,2-a]-pyridine-3-yl-2,5-dioxo-1H-pyrrol-3-yl)-9-fluoro-1,2,3,4-tetrahydro-2-(1-piperidinyl-carbonyl)pyrrolo[3,2,1-jk][1,4]benzodiazepine potentiates the effects of certain chemotherapeutic agents at particular cancers.

BRIEF SUMMARY OF THE INVENTION

The invention provides a method of treating ovarian cancer, non-small cell lung cancer, or colorectal cancer comprising administering to a cancer patient in need of such treatment an effective amount of a chemotherapeutic agent selected from the group consisting of CPT-11, pemetrexed, gemcitabine, etoposide, doxorubicin, and platinum chemotherapeutic agents in combination with an effective amount of 7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinylcarbonyl)-pyrrolo[3,2,1-jk][1,4]benzodiazepine or a pharmaceutically acceptable salt or a solvate thereof.

The invention further provides a method of treating gastric cancer comprising administering to a cancer patient in need of such treatment an effective amount of a chemotherapeutic agent selected from the group consisting of 5-fluorouracil and platinum chemotherapeutic agents in combination with an effective amount of 7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinylcarbonyl)-pyrrolo[3,2,1-jk][1,4]benzodiazepine or a pharmaceutically acceptable salt or a solvate thereof.

The invention also provides the use of 7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinylcarbonyl)-pyrrolo[3,2,1-jk][1,4]benzodiazepine or a pharmaceutically acceptable salt or a solvate thereof for the preparation of a medicament for use in combination with a chemotherapeutic agent selected from the group consisting of CPT-11, pemetrexed, gemcitabine, etoposide, doxorubicin, and platinum chemotherapeutic agents for the treatment of ovarian cancer, non-small cell lung cancer, or colorectal cancer.

The invention also provides the use of 7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinylcarbonyl)-pyrrolo[3,2,1-jk][1,4]benzodiazepine or a pharmaceutically acceptable salt or a solvate thereof for the preparation of a medicament for use in combination with a chemotherapeutic agent selected from the group consisting of 5-fluorouracil and platinum chemotherapeutic agents for the treatment of gastric cancer.

The invention further provides a pharmaceutical composition obtained by the steps comprising:
a) adding 7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinyl-carbonyl)pyrrolo[3,2,1-jk][1,4]benzodiazepine or a pharmaceutically acceptable salt or a solvate thereof to an aqueous solution at a pH less than 5.5 containing at least 1 molar equivalent of SBE7-β-CD and optionally a pharmaceutically acceptable buffer;
b) adjusting the pH of the resulting solution to between 2.5 and 3.5 with a pharmaceutically acceptable acid or base; and
c) optionally lyophilizing the resulting solution.

This invention also provides a pharmaceutical composition capable of reconstitution with water to a solution suitable for administration to a patient by injection or infusion, comprising one molar equivalent of 7-(2,5-dihydro-4-imidazo[1,2-a] pyridine-3-yl-2,5-dioxo-1H-pyrrol-3-yl)-9-fluoro-1,2,3,4-tetrahydro-2-(1-piperidinylcarbonyl)-pyrrolo[3,2,1-jk][1,4] benzodiazepine or a pharmaceutically acceptable salt or solvate thereof, at least one molar equivalent of SBE7-β-CD and optionally a pharmaceutically acceptable buffer.

A further aspect of this invention is a pharmaceutical composition comprising one molar equivalent of 7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinylcarbonyl)-pyrrolo[3,2,1-jk][1,4]benzo-diazepine and at least one molar equivalent of SBE7-β-CD.

Additionally, the invention provides a process for the preparation of a pharmaceutical composition comprising 7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinyl-carbonyl)pyrrolo-[3,2,1-jk][1,4]benzodiazepine that is capable of reconstitution with water to a solution suitable for administration to a patient by injection or infusion, comprising the steps of:

a) adding 7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinyl-carbonyl)pyrrolo[3,2,1-jk][1,4]benzo-diazepine or a pharmaceutically acceptable salt or a solvate thereof to an aqueous solution at a pH less than 5.5 containing at least 1 molar equivalent of SBE7-β-CD and optionally a pharmaceutically acceptable buffer;
 b) adjusting the pH of the resulting solution to between 2.5 and 3.5 with a pharmaceutically acceptable acid or base; and
 c) lyophilizing the resulting solution.

The invention also provides an improved method of using CPT-11, pemetrexed, gemcitabine, etoposide, doxorubicin, and platinum chemotherapeutic agents in the treatment of ovarian cancer, non-small cell lung cancer, or colorectal cancer in a cancer patient in need of such treatment, where the improvement comprises the co-administration of 7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinyl-carbonyl)-pyrrolo[3,2,1-jk][1,4]benzodiazepine or a pharmaceutically acceptable salt or a solvate thereof.

The invention also provides an improved method of using 5-fluorouracil and platinum chemotherapeutic agents in the treatment of gastric cancer in a cancer patient in need of such treatment, where the improvement comprises the co-administration of 7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinyl-carbonyl)-pyrrolo[3,2,1-jk][1,4]benzodiazepine or a pharmaceutically acceptable salt or a solvate thereof.

DETAILED DESCRIPTION OF THE INVENTION

The compound CPT-11 is also known as irinotecan and is sold under the trade name CAMPTOSAR®. CPT-11 is a chemotherapy drug used to treat patients with advanced cancer of the large intestine and colon. It is administered periodically by bolus or infusion injection at a dose of 120-180 mg/m$^2$ during six week treatment cycles. CPT-11 is typically administered in combination with 5-fluorouracil (5-FU) and leucovorin (LV).

The compound pemetrexed is sold under the trade name ALIMTA®. Pemetrexed is a chemotherapy drug used to treat patients with locally advanced or metastatic non-small cell lung cancer after prior chemotherapy. Pemetrexed in combination with cisplatin is indicated for the treatment of patients with malignant pleural mesothelioma whose disease is unresectable or who are otherwise not candidates for curative surgery. Typically 500 mg/m$^2$ of pemetrexed is administered to a patient by infusion over 10 minutes every 21 days after pre-treatment with folic acid, vitamin B$_{12}$ and dexamethasone.

The term "platinum chemotherapeutic agent" is taken to mean a cancer chemotherapeutic agent that contains platinum. Specific platinum chemotherapeutic agents contemplated by the method of this invention include cisplatin, carboplatin, and oxaliplatin. The use of cisplatin or carboplatin is preferred.

The compound cisplatin is sold under the trade name PLATINOL®-AQ. Cisplatin is administered to treat patients with metastatic ovarian tumors who have already received appropriate surgical and/or radiotherapeutic procedures. As a single agent, cisplatin is typically administered at a dose of 100 mg/m$^2$ IV per cycle, once every four weeks. Cisplatin may also be administered in combination with CYTOXAN®.

The compound carboplatin is sold under the trade name PARAPLATIN®. Carboplatin is administered to treat patients with ovarian carcinoma. As a single agent, carboplatin is typically administered at a dose of 360 mg/m$^2$ IV per cycle, once every four weeks. Carboplatin may also be administered with cyclophosphamide.

The compound oxaliplatin is sold under the trade name ELOXATIN®. Oxaliplatin is administered to treat patients with colorectal cancer. It is typically administered at a dose of 85 mg/m$^2$ IV per cycle, once every two weeks in combination with 5-FU and LV.

The compound doxorubicin is sold under the trade names ADRIAMYCIN® and RUBEX®. Doxorubicin has been used successfully to produce regression in disseminated neoplastic conditions such as acute lymphoblastic leukemia, acute myeloblastic leukemia, Wilms' tumor, neuroblastoma, soft tissue and bone sarcomas, breast carcinoma, ovarian carcinoma, transitional cell bladder carcinoma, thyroid carcinoma, gastric carcinoma, Hodgkin's disease, malignant lymphoma and bronchogenic carcinoma. It is typically administered at a dose of 60-75 mg/m$^2$ IV at 21-day intervals.

The compound etoposide is sold under the trade names ETOPOPHOS®, TOPOSAR® and VEPESID®. Etoposide is administered to treat patients with testicular or lung cancer. It is typically administered by injection at a dose of from 5-100 mg/m$^2$.

The compound 5-fluorouracil (5-FU) is sold under the trade name ADRUCIL®. It is administered to treat patients with carcinoma of the colon, rectum, breast, stomach and pancreas. 5-FU is typically administered IV at a dose of 12 mg/kg once daily for four successive days.

Gemcitabine is sold under the trade name GEMZAR®. It is most commonly used to treat non-small cell lung cancer, pancreatic cancer, bladder cancer, and breast cancer. It is typically administered by IV infusion at a dose of 1000 mg/m$^2$ over 30 minutes weekly for 3 consecutive weeks out of 4 weeks.

The skilled artisan will appreciate that the exact dosage and number of treatment cycles of any of the agents described above required to treat a patient are determined by a physician in view of the stage and severity of the disease as well as the specific needs and response of an individual patient.

The compound 7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinyl-carbonyl)-pyrrolo[3,2,1-jk][1,4]benzodiazepine is taught to be an inhibitor of GSK-3β in WO 03/076442, where it is referred to as 3-(9-fluoro-6-(piperidin-1-yl)carbonyl)-6,7-dihydro-6H-[1,4]diazepino-[6,7,1-hi]indol-1-yl)-4-(imidazo[1,2-a]pyridin-3-yl)-2,5-dioxopyrrole (Example 365, page 113). The two naming conventions described above are taken to be synonymous and each is taken to identify the following structure:

Compound I

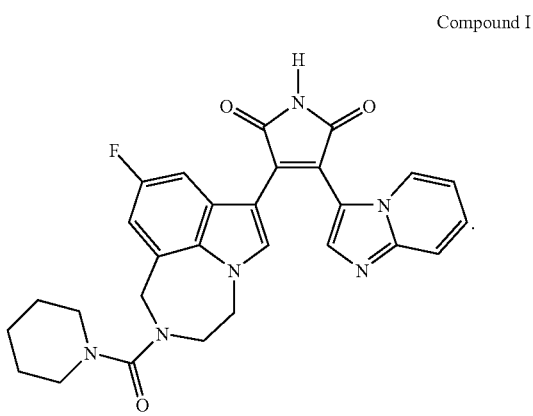

Compound I is a base, and accordingly may react with any of a number of inorganic and organic acids to form pharmaceutically acceptable acid addition salts. Preferred pharmaceutically acceptable salts are those formed with HCl, HBr, sulfuric acid, or methanesulfonic acid.

Compound I forms solvates with, for example, water, methanol, and ethanol. A preferred solvate is that formed with ethanol.

Although Compound I lacks useful antitumor activity in its own right, when administered in combination with CPT-11, pemetrexed, gemcitabine, etoposide, doxorubicin, or platinum chemotherapeutic agents, a significant therapeutic benefit in the treatment of ovarian, non-small cell lung, or colorectal cancer is realized relative to treatment with CPT-11, pemetrexed, gemcitabine, etoposide, doxorubicin, or platinum chemotherapeutic agents alone. One benefit of this combination is that the therapeutic effect of CPT-11, pemetrexed, gemcitabine, etoposide, doxorubicin, and platinum chemotherapeutic agents is potentiated by co-administration with Compound I. That is, a lower dose of CPT-11, pemetrexed, gemcitabine, etoposide, doxorubicin, or platinum chemotherapeutic agents than is typically administered will provide a similar therapeutic effect to the patient. Furthermore, a greater therapeutic effect of CPT-11, pemetrexed, gemcitabine, etoposide, doxorubicin, or platinum chemotherapeutic agents will be realized by the patient at the typical dose when these agents are co-administered with Compound I. This method of treatment provides the further advantage of convenience for the patient and physician, allowing administration of Compound I in the same treatment schedule as CPT-11, pemetrexed, gemcitabine, etoposide, doxorubicin, or platinum chemotherapeutic agents.

The combination therapy of this invention is an improved method of treating a patient suffering from ovarian cancer, non-small cell lung cancer, or colorectal cancer. The patient is a mammal and the preferred mammal is a human.

Although all of the described combinations of Compound I or a pharmaceutically acceptable salt or solvate thereof and chemotherapeutic agents are useful, certain combinations are preferred. One preferred combination is the co-administration of 7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinyl-carbonyl)-pyrrolo[3,2,1-jk][1,4]benzodiazepine or a pharmaceutically acceptable salt or solvate thereof with a platinum chemotherapeutic agent. Another embodiment is the co-administration of 7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinyl-carbonyl)-pyrrolo[3,2,1-jk][1,4]benzodiazepine or a pharmaceutically acceptable salt or solvate thereof with either cisplatin or carboplatin. A further embodiment of the invention is the administration of 7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinyl-carbonyl)-pyrrolo[3,2,1-jk][1,4]benzodiazepine or a pharmaceutically acceptable salt or solvate thereof with pemetrexed and a platinum chemotherapeutic agent. It is preferred that 7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinyl-carbonyl)-pyrrolo[3,2,1-jk][1,4]benzodiazepine or a pharmaceutically acceptable salt or solvate thereof be administered with pemetrexed and carboplatin.

The phrase "an effective amount of a chemotherapeutic agent" is taken to mean the dosage of the particular chemotherapeutic agent necessary to either destroy the target cancer cells or slow or arrest the progression of the cancer in a patient when the chemotherapeutic agent is administered in combination with Compound I or a pharmaceutically acceptable salt or a solvate thereof.

The phrase "an effective amount of 7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinylcarbonyl)-pyrrolo[3,2,1-jk][1,4]benzodiazepine or a pharmaceutically acceptable salt or a solvate thereof" is taken to mean the dosage of Compound I or a pharmaceutically acceptable salt or a solvate thereof necessary to potentiate the effect of a specific dose of a particular chemotherapeutic agent in order to either destroy the target cancer cells or slow or arrest the progression of the cancer in a patient. Anticipated dosages of Compound I or a pharmaceutically acceptable salt or a solvate thereof are in the range of 5 to 600 mg/patient/day. Preferred dosages are in the range of 50 to 400 mg/patient/day. Most preferred dosages are in the range of 100 to 400 mg/patient/day. The exact dosage required to treat a patient will be determined by a physician in view of the stage and severity of the disease as well as the specific needs and response of the individual patient.

The phrase "to potentiate the effect of a specific dose of a particular chemotherapeutic agent" is taken to mean that a lower dose of a chemotherapeutic agent than is typically administered will be an effective dose, or that a greater therapeutic effect of the chemotherapeutic agent is realized by the patient at the typical dose when it is co-administered with Compound I or a pharmaceutically acceptable salt or solvate thereof.

The terms "co-administered" and "co-administration" as well as the phrases "in combination with" and "administered in combination with" as used herein are taken to mean that Compound I or a pharmaceutically acceptable salt or solvate thereof is given to the patient during the same treatment cycle as CPT-11, pemetrexed, or a platinum chemotherapeutic agent. That is, Compound I or a pharmaceutically acceptable salt or solvate thereof may be administered prior to, during, or after the administration of CPT-11, pemetrexed, or a platinum chemotherapeutic agent at the discretion of the physician taking into account the tumor type, the stage of the disease, the specific chemotherapeutic agent employed, and the condition and sensitivity of the patient.

The following in vitro and in vivo studies demonstrate the advantages of these combinations.

In Vitro Efficacy Examples

Apoptosis or programmed cell death is characterized by a set of biochemical reactions, one of which is the induction of caspases. Activated caspases are proteases that participate in a cascade of cleavage events that disable key enzymes responsible for cell homeostasis and repair. Caspases 3 and 7 play key effector roles in apoptosis and can be detected and measured by a fluorescent biochemical assay. The increase of Caspase-3/7 activity in cells is directly correlated to apoptotic activity. (D. W. Nicholson, et al., Nature, 376, 37-43 (1995)) The Promega Apo-ONE Homogeneous Caspase-3/7 Assay Kit was used (Catalog #G7791). The assay buffer consists of 30 mM HEPES (N-(2-hydroxyethyl)piperazine-N'-(2-ethanesulfonic acid) pH 7.4, 150 mM NaCl, 50 mM KCl, 10 mM $MgCl_2$, 0.4 mM EGTA (ethylene glycol tetraacetic acid), 0.5% Nonidet P40 (octylphenolpoly(ethyleneglycol ether)), 0.1% CHAPS (3-[(3-Cholamidopropyl)dimeth-ylammonio]-1-propanesulfonate hydrate and 10% sucrose, which lyses/permeabilizes cultured cells and a caspase 3/7 substrate, Z-DEVD (Z-Asp(OMe)-Glu(OMe)-Val-Asp(OMe)), coupled to a profluorescent rhodamine 110. When the buffer-substrate mixture is added to a test sample, the cleavage and subsequent removal of the DEVD peptides by caspase 3/7 activity results in intense fluorescence of the rhodamine 110 leaving group, which is detected by excitation at 499 nm. The amount of fluorescent product is proportional to the amount of caspase 3/7 cleavage activity in the sample.

To measure the apoptotic effect of test compounds, tumor cells are plated at $1 \times 10^4$ cells per well in 96 well plates and incubated overnight at 37° C., with 5% $CO_2$. Tumor cells are treated with test compound at desired concentrations in triplicate, including untreated/negative control wells. The assay plates are re-incubated for 48 hrs. At the end of the incubation period, a mixture of the assay buffer and substrate is added to each sample well. The fluorescence in each well is measured at an excitation wavelength of 485+/−20 nm and an emission wavelength of 530+/−25 nm. The % increase of caspase activity in treated cells is calculated relative to untreated controls.

HCT-116 and colo-205 are colorectal carcinomas, A2780 and SKOV3 are ovarian carcinomas, A549, Calu-6, and NCI H-460 are non-small cell lung carcinomas, and AGS, KATO III, and MKN 45 are gastric carcinomas. In the following tables the term "Compound I" or "Cmpd I" are taken to mean 7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinyl-carbonyl)-pyrrolo[3,2,1-jk][1,4]benzodiazepine.

The chemotherapeutic agents were tested at the following concentrations:

| Cell Line | Cisplatin | Carboplatin | CPT-11 | Pemetrexed |
|---|---|---|---|---|
| HCT-116 | 5 µM | — | 20 nM | 60 nM |
| Colo-205 | 5 µM | — | 20 nM | — |
| A2780 | 5 µM | — | 20 nM | 60 nM |
| A549 | 1 µM | 10 µM | — | — |
| NCI-H460 | 1 µM | 10 µM | — | — |
| Calu-6 | — | — | — | 60 nM |

The data in Tables 1-12 are expressed as % increase of caspase activity relative to untreated controls unless otherwise noted.

TABLE 1

Cisplatin in Combination with Compound I

| Cell Line | Culture medium | Compound I* | cis-platin | Compound I* + cisplatin | Fold increase over cisplatin |
|---|---|---|---|---|---|
| HCT-116 | 0 | 16 | 36 | 180 | 5 |
| Colo-205 | 0 | 12 | 8 | 85 | 10.6 |
| A2780 | 0 | 0 | 1.5 | 93 | 62 |
| A549 | 0 | 80 | 4 | 183 | 46 |
| NCI-H460 | 0 | 99 | 47 | 379 | 8 |

*Concentration of Compound I varied by cell line: HCT-116 (300 nM); Colo-205 (110 nM); A2780 (60 nM); A549 (300 nM); NCI-H460 (300 nM)

TABLE 2

Carboplatin in Combination with Compound I

| Cell Line | Culture medium | Compound I* | carbo-platin | Compound I* + carboplatin | Fold increase over carboplatin |
|---|---|---|---|---|---|
| A549 | 0 | 52 | 14 | 282 | 20.1 |
| NCI-H460 | 0 | 122 | 16 | 299 | 18.7 |

*Concentration of Compound I varied by cell line: A549 (300 nM); NCI-H460 (100 nM)

TABLE 3

CPT-11 in Combination with Compound I

| Cell Line | Culture medium | Compound I* | CPT-11 | Compound I* + CPT-11 | Fold increase over CPT-11 |
|---|---|---|---|---|---|
| HCT-116 | 4 | 53 | 50 | 263 | 5.3 |
| Colo-205 | 0 | 45 | 38 | 254 | 6.7 |
| A2780 | 1 | 1 | 153 | 450 | 2.9 |

*Concentration of Compound I varied by cell line: HCT-116 (330 nM); Colo-205 (33 nM); A2780 (330 nM)

TABLE 4

Pemetrexed in Combination with Compound I

| Cell Line | Culture medium | Compound I* | Peme-trexed | Compound I* + Pemetrexed | Fold increase over Pemetrexed |
|---|---|---|---|---|---|
| HCT-116 | 0 | 0 | 23 | 125 | 5.4 |
| Calu-6 | 0 | 139 | 24 | 319 | 13.3 |
| A2780 | 0 | 10 | 0 | 35 | —** |

*Concentration of Compound I was 30 nM for all cell lines
**Cannot be calculated, no measured effect of pemetrexed alone.

TABLE 5

HCT-116

| Drug | Cmpd I Conc. | Drug Conc. | Cmpd I | Drug | Compound I + Drug | Fold Increase Over Drug |
|---|---|---|---|---|---|---|
| 5-FU | 12 nM | 5 µM | 47 | 55 | 305 | 5.5 |
| Gemcita-bine | 60 nM | 30 nM | 0 | 324 | 595 | 1.8 |

TABLE 6

A2780

| Drug | Cmpd I Conc. | Drug Conc. | Cmpd I | Drug | Compound I + Drug | Fold Increase Over Drug |
|---|---|---|---|---|---|---|
| Carboplatin* | 300 nM | 5 μM | 55 | 78 | 237 | 3 |

*Plates incubated for 72 hours.

TABLE 7

SKOV3

| Drug | Cmpd I Conc. | Drug Conc. | Cmpd I | Drug | Compound I + Drug | Fold Increase Over Drug |
|---|---|---|---|---|---|---|
| Doxorubicin | 300 nM | 1 μM | 0 | 184 | 270 | 1.5 |

TABLE 8

Calu 6

| Drug | Cmpd I Conc. | Drug Conc. | Cmpd I | Drug | Compound I + Drug | Fold Increase Over Drug |
|---|---|---|---|---|---|---|
| Cisplatin | 33 nM | 2 μM | 154 | 97 | 471 | 4.8 |

TABLE 9

NCI H-460

| Drug | Cmpd I Conc. | Drug Conc. | Cmpd I | Drug | Compound I + Drug | Fold Increase Over Drug |
|---|---|---|---|---|---|---|
| Pemetrexed | 300 nM | 500 nM | 38 | 185 | 872 | 4.7 |
| Gemcitabine | 300 nM | 50 nM | 186 | 1187 | 1996 | 1.7 |
| Etoposide | 300 nM | 1 μM | 222 | 251 | 935 | 3.7 |

TABLE 10

AGS

| Drug | Cmpd I Conc. | Drug Conc. | Cmpd I | Drug | Compound I + Drug | Fold Increase Over Drug |
|---|---|---|---|---|---|---|
| Cisplatin* | 900 nM | 5 μM | 0 | 147 | 208 | 1.4 |
| 5-FU | 900 nM | 3 μM | 0 | 133 | 235 | 1.7 |

*Plates incubated for 72 hours.

TABLE 11

KATO III

| Drug | Cmpd I Conc. | Drug Conc. | Cmpd I | Drug | Compound I + Drug | Fold Increase Over Drug |
|---|---|---|---|---|---|---|
| Cisplatin | 600 nM | 10 μM | 48 | 389 | 631 | 1.6 |

TABLE 12

MKN 45

| Drug | Cmpd I Conc. | Drug Conc. | Cmpd I | Drug | Compound I + Drug | Fold Increase Over Drug |
|---|---|---|---|---|---|---|
| Cisplatin | 600 nM | 10 μM | 162 | 359 | 868 | 2.4 |
| 5-FU* | 300 nM | 5 μM | 105 | 415 | 777 | 1.9 |

*Plates incubated for 72 hours.

The fold increase data in Tables 1-12 reflects the potentiation of chemotherapeutic drug-mediated apoptosis in cells by the co-administration of Compound I relative to the apoptotic effect of the chemotherapeutic drug alone.

In Vivo Efficacy Experiments

Cultured cells are implanted subcutaneously in the rear flank of female CD-1 nu/nu strain mice which have been acclimated for one week in the animal facility after receipt from the vendor. Mice are randomized into groups of 7 or 8 mice per group and treatment begun when the mean tumor volume reaches ~100 mm$^3$ Compound I is dosed IV and the chemotherapeutic agent is given IP. When the agents are given in combination, the chemotherapeutic agent is dosed 60 minutes prior to Compound I. The tumors are measured 2 times per week by electronic calipers to plot growth curves. Tumor growth delay is the increase in median time it takes for a tumor to reach 1000 mm$^3$ in volume when compared to a control group. Animals are also monitored for fluctuations in body weight and survival.

TABLE 13

Cisplatin in Combination with Compound I in A2780 human ovarian carcinoma xenografts

| Treatment Group | Tumor Growth Delay Mean ± Standard Error (Days) | p-Value** |
|---|---|---|
| Captisol vehicle | 0 ± 1.2 | — |
| Saline vehicle | 0.5 ± 1.4 | — |
| Compound I (5 mg/kg) | −0.3 ± 1.4 | — |
| Cisplatin (5 mg/kg) | 5 ± 1.6 | — |
| Compound I + cisplatin* | 23.9 ± 3.9 | <0.001 |

5 mg/kg cisplatin is dosed IP alone and in combination with 5 mg/kg Compound I (injected IV). Compound I at 5 mg/kg (injected IV), is also dosed alone as a control group. Animals received 3 consecutive cycles of cisplatin and Compound I, each cycle separated by 7 days.
*5 mg/kg of each of cisplatin and Compound I
**Effect of combination relative to cisplatin alone

TABLE 14

Cisplatin in Combination with Compound I in HCT-116 human colorectal carcinoma xenografts

| Treatment Group | Tumor Growth Delay Mean ± Standard Error (Days) | p-Value** |
|---|---|---|
| Captisol vehicle | 0 ± 5.9 | — |
| Saline vehicle | 3.8 ± 4.5 | — |
| Compound I (5 mg/kg) | 2 ± 2.2 | — |
| Cisplatin (10 mg/kg) | 23 ± 10.3 | — |
| Compound I + cisplatin* | 40.7 ± 8.3 | <0.01 |

10 mg/kg cisplatin is dosed IP alone and in combination with 5 mg/kg Compound I (injected IV). Compound I at 5 mg/kg (injected IV), is also dosed alone as a control group. Animals received 3 consecutive cycles of cisplatin and LY2090314, each cycle separated by 7 days.
*5 mg/kg of Compound I and 10 mg/kg cisplatin
**Effect of combination relative to cisplatin alone

TABLE 15

Cisplatin in Combination with Compound I in Colo-205 human colorectal carcinoma xenografts

| Treatment Group | Tumor Growth Delay Mean ± Standard Error (Days) | p-Value** |
|---|---|---|
| Captisol vehicle | 0 ± 1.4 | — |
| Saline vehicle | 4.8 ± 2.1 | — |
| Compound I (5 mg/kg) | 10.9 ± 2.2 | — |
| Cisplatin (5 mg/kg) | 18 ± 3.5 | — |
| Compound I + cisplatin* | 31.5 ± 18.6 | <0.001 |

5 mg/kg cisplatin is dosed IP alone and each in combination with 5 mg/kg Compound I (injected IV). Compound I at 5 mg/kg (injected IV), is also dosed alone as a control group. Animals received 3 consecutive cycles of cisplatin and Compound I, each cycle separated by 7 days.
*5 mg/kg of each of cisplatin and Compound I
**Effect of combination relative to cisplatin alone

TABLE 16

Carboplatin in Combination with Compound I in NCI-H460 human non-small cell lung cancer xenografts

| Treatment Group | Tumor Growth Delay Mean ± Standard Error (Days) | p-Value** |
|---|---|---|
| Captisol vehicle | 2.4 ± 0 | — |
| Saline vehicle | 2.9 ± 2.7 | — |
| Compound I (5 mg/kg) | 3 ± 1.4 | — |
| Carboplatin (50 mg/kg) | 2 ± 2.9 | — |
| Compound I + carboplatin* | 8.6 ± 13.5 | <0.01 |

Compound I is dosed IV at 5 mg/kg alone and with 50 mg/kg Carboplatin IP. Dosing is every 14 days × 3 cycles. For treatment groups receiving both Compound I and Carboplatin, Carboplatin is administered 60 minutes prior to Compound I.
*50 mg/kg carboplatin and 5 mg/kg of Compound I
**Effect of combination relative to carboplatin alone

TABLE 17

Carboplatin and Pemetrexed in Combination with Compound I in NCI-H460 human non-small cell lung cancer xenografts

| Treatment Group | Tumor Growth Delay Mean ± Standard Error (Days) | p-Value* |
|---|---|---|
| Captisol vehicle | 0 ± 3.4 | — |
| Saline vehicle | 2.7 ± 3.8 | — |
| Compound I (5 mg/kg) | 1.4 ± 3.8 | — |
| Pemetrexed (300 mg/kg) + Carboplatin (10 mg/kg) | 2.8 ± 2.8 | — |
| Pemetrexed (300 mg/kg) + Compound I (5 mg/kg) | 3.1 ± 3.3 | — |
| Pemetrexed (300 mg/kg) + Carboplatin (10 mg/kg) + Compound I (5 mg/kg) | 10.5 ± 3.8 | <0.01 |

Compound I is dosed IV at 5 mg/kg alone, with 10 mg/kg carboplatin IP, with 300 mg/kg pemetrexed IP, and with 10 mg/kg carboplatin IP and 300 mg/kg pemetrexed IP. Dosing is every 14 days for 3 cycles. For treatment groups receiving both Compound I and carboplatin, carboplatin is administered 60 minutes prior to Compound I. For treatment groups receiving both Compound I and pemetrexed, pemetrexed is administered 24 hours prior to compound I administration. For treatment groups receiving Compound I, carboplatin and pemetrexed, pemetrexed is administered 24 hours before Compound I and carboplatin is administered 60 minutes before compound I.
*Effect of pemetrexed, carboplatin, and Compound I relative to carboplatin + pemetrexed The data in Tables 13-17 demonstrate that the potentiation of chemotherapeutic drug-induced tumor growth delay by Compound I is statistically significant relative to the tumor growth delay caused by the chemotherapeutic drugs alone.

Preparation 1

2-imidazo[1,2-a]pyridin-3-yl-acetamide

4,4-Dimethoxy-but-2-enoic acid ethyl ester

Add potassium carbonate (16.5 g, 120 mmol) to a solution of dimethoxy acetaldehyde (60% wt. in water) (15 mL, 100 mmol) and triethyl phosphonoacetate (20 mL, 100 mmol) in 210 mL tetrahydrofuran and 30 mL water. Stir the mixture at room temperature for 4 hours. Pour the reaction mixture into diethyl ether (200 mL) and wash with saturated aqueous sodium chloride. Dry the organic phase over sodium sulfate and concentrate under reduced pressure to provide the desired compound as a yellow oil (15.8 g, 90%).
$^1$H-NMR (300 MHz, CDCl$_3$): δ 6.77 (dd, J=15.9, 4.0 Hz, 1H), 6.13 (dd, J=15.9, 1.4 Hz, 1H), 4.95 (dd, J=4.0, 1.4 Hz, 1H), 4.22 (q, J=7.1 Hz, 2H), 3.34 (s, 6H), 1.30 (t, J=7.1 Hz, 3H).

Imidazo[1,2-α]pyridin-3-yl-acetic acid ethyl ester

Heat a mixture of 4,4-dimethoxy-but-2-enoic acid ethyl ester (43.5 g, 250 mmol) and p-toluenesulfonic acid (4.75 g, 25 mmol) in acetonitrile (240 mL) and water (15 mL) at reflux for 2 hours. Cool the reaction mixture to room temperature and add 2-aminopyridine (18.8 g, 200 mmol). Heat the mixture at reflux for 16 hours then cool to room temperature. Dilute the reaction mixture with ethyl acetate (1200 mL) and wash sequentially with saturated aqueous sodium bicarbonate (600 mL×3) and saturated aqueous sodium chloride (600 mL×2). Dry the organic phase over sodium sulfate and concentrate under reduced pressure to provide the desired compound as a brown oil (30 g, 73%).
$^1$H-NMR (300 MHz, CDCl$_3$): δ 8.06 (d, J=6.6 Hz, 1H), 7.63 (d, J=9.1 Hz, 1H), 7.56 (s, 1H), 7.20 (dd, J=8.9, 6.8 Hz, 1H), 6.84 (t, J=6.7 Hz, 1H), 4.17 (q, J=7.3 Hz, 2H), 3.93 (s, 2H), 1.25 (t, J=7.3 Hz, 3H).

Amide Formation

Heat a solution of imidazo[1,2-α]pyridin-3-yl-acetic acid ethyl ester (30 g, 147 mmol) in NH$_3$/MeOH (7 N solution, 250 mL) at 85° C. in a sealed tube for 15 hours. Cool the reaction mixture to room temperature and concentrate under reduced pressure. Treat the residue with dichloromethane, sonicate, and filter the resulting precipitate to provide the desired compound as a yellow solid (8.9 g, 35%).
$^1$H-NMR (300 MHz, DMSO): δ 8.30 (d, J=6.9 Hz, 1H), 7.62 (br s, 1H), 7.54 (d, J=9.0 Hz, 1H), 7.42 (s, 1H), 7.21 (dd, J=7.7, 6.7 Hz, 1H), 7.18 (br s, 1H), 6.91 (t, J=6.8 Hz, 1H), 3.81 (s, 2H).

Preparation 2

9-Fluoro-7-methoxyoxalyl-3,4-dihydro-1H-[1,4]diazepino[6,7,1-hi]indole-2-carboxylic acid tert-butyl ester

2-Dibutoxymethyl-4-fluoro-1-nitro-benzene

Heat a solution of 5-fluoro-2-nitro-benzaldehyde (10 g, 59.17 mmol), butanol (20 mL, 219 mmol) and p-toluenesulfonic acid (600 mg, 3.15 mmol) in toluene (200 mL) at reflux for 2 hours in a flask equipped with a Dean-Stark trap. Cool the reaction mixture to room temperature, dilute with ethyl acetate (400 mL), and wash sequentially with saturated aqueous sodium bicarbonate (300 mL×3) and saturated aqueous sodium chloride (300 mL×2). Dry the organic phase over sodium sulfate and concentrate under reduced pressure to provide the desired compound as a pale yellow oil (17 g, 96%).
$^1$H-NMR (300 MHz, CDCl$_3$): δ 7.91 (dd, J=8.9, 4.9 Hz, 1H), 7.53 (dd, J=9.3, 2.9 Hz, 1H), 7.15-7.09 (m, 1H), 6.04 (s, 1H), 3.67-3.50 (m, 4H), 1.63-1.54 (m, 4H), 1.44-1.32 (m, 4H), 0.92 (t, J=7.3 Hz, 6H).

5-Fluoro-1H-indole-7-carbaldehyde

Add vinylmagnesium bromide (1 M in tetrahydrofuran, 85.2 mL, 85.2 mmol) dropwise to a solution of 2-dibutoxymethyl-4-fluoro-1-nitro-benzene (8.5 g, 28.4 mmol) in tetrahydrofuran (250 mL) at −78° C. Warm the reaction mixture −45° C. to −50° C. for 30 minutes, cool to −78° C., and add vinylmagnesium bromide (1 M in tetrahydrofuran, 85.2 mL, 85.2 mmol) dropwise. Warm the reaction mixture to −45° C. to −50° C. for 20 minutes, then add saturated aqueous ammonium chloride (300 mL). Warm the mixture to room temperature and extract with diethyl ether (200 mL×2). Wash the combined organic phases with saturated aqueous sodium chloride (400 mL×2), dry over sodium sulfate, and concentrate under reduced pressure. Dissolve the residue in tetrahydrofuran (100 mL), add 0.5 N HCl (10 mL), and stir for 20 minutes. Dilute the mixture with diethyl ether (200 mL), wash sequentially with saturated aqueous sodium bicarbonate (200 mL×3) and saturated aqueous sodium chloride (200 mL×2). Dry the organic phase over sodium sulfate and concentrate under reduced pressure. Subject the residue to silica gel chromatography, eluting with 5% to 10% ethyl acetate in hexanes to provide the desired compound as a pale yellow solid (2.6 g, 56%).

$^1$H-NMR (300 MHz, CDCl$_3$): δ 10.07 (s, 1H), 10.05 (br s, 1H), 7.62 (d, J=7.6 Hz, 1H), 7.42-7.39 (m, 2H), 6.60 (d, J=5.4 Hz, 1H).

2-[(5-Fluoro-1H-indol-7-ylmethyl)-amino]-ethanol

Add 2-aminoethanol (1.93 mL, 32.0 mmol) followed by acetic acid (2.01 mL, 48.0 mmol) to a solution of 5-fluoro-1H-indole-7-carbaldehyde (2.6 g, 16.0 mmol) in 1,2-dichloroethane (40 mL). Stir at room temperature for 15 minutes. Add sodium triacetoxyborohydride (4.07 g, 19.2 mmol) portionwise. Stir the reaction mixture at room temperature for 3 hours. Add saturated aqueous sodium bicarbonate (100 mL) slowly followed by 1 N NaOH to pH ~9. Extract with ethyl acetate (100 mL×3). Wash the organic phase with saturated aqueous sodium chloride (200 mL×2), dry over sodium sulfate, and concentrate under reduced pressure to provide the desired compound as a pale yellow solid (3.2 g, 96%).

$^1$H-NMR (300 MHz, CDCl$_3$): δ 9.71 (br s, 1H), 7.24 (d, J=2.7 Hz, 1H), 7.19 (dd, J=9.5, 2.3 Hz, 1H), 6.79 (dd, J=9.8, 2.2 Hz, 1H), 6.49 (dd, J=3.1, 2.2 Hz, 1H), 4.15 (s, 2H), 3.77 (t, J=5.2 Hz, 2H), 2.84 (t, J=5.2 Hz, 2H).

(5-Fluoro-1H-indol-7-ylmethyl)-(2-hydroxy-ethyl)-carbamic acid tert-butyl ester Add a solution of di-tert-butyl dicarbonate (3.63 g, 16.65 mmol) in tetrahydrofuran (40 mL) dropwise to a solution of 2-[(5-fluoro-1H-indol-7-ylmethyl)-amino]-ethanol (3.15 g, 15.14 mmol) in tetrahydrofuran (60 mL) at 0° C. Stir the reaction mixture at room temperature for 2 hours. Add ethyl acetate (200 mL) and wash with saturated aqueous sodium chloride. Dry the organic phase over sodium sulfate and concentrate under reduced pressure to provide the desired compound as a pale yellow oil (4.9 g, >100%).

$^1$H-NMR (300 MHz, CDCl$_3$): δ 10.17 (br s, 1H), 7.27-7.23 (m, 2H), 6.81 (dd, J=9.4, 2.4 Hz, 1H), 6.50 (dd, J=2.9, 2.2 Hz, 1H), 4.67 (s, 2H), 3.72 (br s, 2H), 3.33 (t, J=5.3 Hz, 2H), 1.50 (s, 9H).

Methanesulfonic acid 2-[tert-butoxycarbonyl-(5-fluoro-1H-indol-7-ylmethyl)-amino]-ethyl ester Add triethylamine (4.64 mL, 33.3 mmol) followed by methanesulfonyl chloride (1.29 mL, 16.65 mmol) to a solution of (5-fluoro-1H-indol-7-ylmethyl)-(2-hydroxyethyl)-carbamic acid tert-butyl ester (4.9 g, assume 15.14 mmol) in dichloromethane (70 mL) at 0° C. Stir the reaction mixture for 30 minutes at 0° C. Dilute with ethyl acetate (200 mL), wash with sequentially with saturated aqueous sodium bicarbonate (200 mL×3) and saturated aqueous sodium chloride (200 mL×2). Dry the organic phase over sodium sulfate and concentrate under reduced pressure to provide the desired compound as a yellow brown oil (5.9 g, >100%).

$^1$H-NMR (300 MHz, CDCl$_3$): δ 10.07 (br s, 1H), 7.28-7.2 (m, 2H), 6.83 (dd, J=9.3, 2.3 Hz, 1H), 6.50 (dd, J=2.9, 2.2 Hz, 1H), 4.67 (s, 2H), 4.17 (t, J=5.5 Hz, 2H), 3.51 (t, J=5.6 Hz, 2H), 2.79 (s, 3H), 1.51 (s, 9H).

9-Fluoro-3,4-dihydro-1H-[1,4]diazepino[6,7,1-hi]indole-2-carboxylic acid tert-butyl ester Add sodium hydride (60%) (666 mg, 16.65 mmol) in one portion to a solution of methanesulfonic acid 2-[tert-butoxycarbonyl-(5-fluoro-1H-indol-7-ylmethyl)-amino]-ethyl ester (5.9 g, assume 15.14 mmol) in dimethylformamide (40 mL) at 0° C. Stir the reaction mixture at 0° C. for 10 minutes and then at room temperature for 30 minutes. Add water (200 mL) slowly. Filter and dry the resulting yellow precipitate to provide the desired compound (4.14 g, 94%).

$^1$H-NMR (300 MHz, CDCl$_3$): δ 7.15 (d, J=9.1 Hz, 1H), 7.07 (s, 1H), 6.78 (dd, J=14.7, 8.8 Hz, 1H), 6.49 (d, J=3.1 Hz, 1H), 4.81 (s, 1H), 4.76 (s, 1H), 4.25-4.23 (m, 2H), 3.94-3.83 (m, 2H), 1.49 (s, 9H).

9-Fluoro-7-methoxyoxalyl-3,4-dihydro-1H-[1,4]diazepino[6,7,1-hi]indole-2-carboxylic acid tert-butyl ester Add oxalyl chloride (1.62 mL, 18.56 mmol) to a solution of 9-fluoro-3,4-dihydro-1H-[1,4]diazepino[6,7,1-hi]indole-2-carboxylic acid tert-butyl ester (4.14 g, 14.28 mmol) in methyl tert-butyl ether (100 mL) at −5° C. Warm the reaction mixture to room temperature over 1.5 hours and then cool to −5° C. Add methanol (11.6 mL, 286 mmol) and stir at −5° C. for 30 minutes. Add saturated aqueous sodium bicarbonate (100 mL) and extract with ethyl acetate (100 mL×3). Wash the combined organic phase sequentially with saturated aqueous sodium bicarbonate (200 mL×3) and saturated aqueous sodium chloride (200 mL×2). Dry the organic phase over sodium sulfate and then concentrate under reduced pressure to provide the title compound as a yellow solid (5.13 g, 93%).

$^1$H-NMR (300 MHz, CDCl$_3$): δ 8.38 (s, 1H), 8.04 (d, J=6.8 Hz, 1H), 6.89 (dd, J=19.7, 8.6 Hz, 1H), 4.90 (s, 1H), 4.81 (s, 1H), 4.45-4.43 (m, 2H), 4.05-3.93 (m, 2H), 3.95 (s, 3H), 1.42 (s, 9H).

Preparation 3

3-(9-Fluoro-1,2,3,4-tetrahydro-[1,4]diazepino[6,7,1-hi]indol-7-yl)-4-imidazo[1,2-a]-pyridin-3-yl-pyrrole-2,5-dione dihydrochloride Add potassium tert-butoxide (4.58 g, 40.92 mmol) in one portion to a solution of 9-fluoro-7-methoxyoxalyl-3,4-dihydro-1H-[1,4]diazepino[6,7,1-hi]indole-2-carboxylic acid tert-butyl ester (5.13 g, 13.64 mmol) and 2-imidazo[1,2-a]pyridin-3-yl-acetamide (2.39 g, 13.64 mmol) in dimethylformamide (80 mL). Stir the reaction mixture at room temperature for three hours. Add saturated aqueous ammonium chloride (200 mL) and extract with ethyl acetate (200 mL×3). Wash the combined organic phases with saturated aqueous sodium chloride (200 mL×3), dry over sodium sulfate, and concentrate under reduced pressure. Dissolve the residue in dichloromethane (20 mL) and add 4N HCl in dioxane (40 mL) dropwise, then stir at room temperature for 4 hours. Filter the resulting precipitate and wash with diethyl ether to provide the title compound as a red solid (4.4 g, 68%).

MS (APCI): m/z=402 $[C_{22}H_{16}FN_5O_2+H]^+$.

Example 1

7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinyl-carbonyl)-pyrrolo[3,2,1-jk][1,4]benzodiazepine Add piperidine-1-carbonyl chloride (0.5 mL, 4.0 mmol) to a solution of 3-(9-fluoro-1,2,3,4-tetrahydro-[1,4]diazepino[6,7,1-hi]indol-7-yl)-4-imidazo[1,2-a]pyridin-3-yl-pyrrole-2,5-dione (1.42 g, 3.0 mmol) and triethylamine (2.09 mL, 15.0 mmol) in methanol (80 mL). Stir at room temperature over night. Add triethylamine (1.04 mL, 7.5 mmol) and piperidine-1-carbonyl chloride (0.5 mL, 4.0 mmol). Stir at room temperature for 5 hours. Add ethyl acetate (500 mL) and wash sequentially with saturated aqueous sodium bicarbonate (300 mL×3) and saturated aqueous sodium chloride (200 mL). Dry the organic phase over sodium sulfate and concentrate under reduced pressure. Subject the residue to silica gel chromatography, eluting with 0% to 3% methanol in ethyl acetate to provide the title compound as a red solid (700 mg, 45%).

m.p.=188-190° C.

MS (APCI): m/z=513 $[C_{28}H_{25}FN_6O_3+H]^+$.

Example 2

7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinyl-carbonyl)-pyrrolo[3,2,1-jk][1,4]benzodiazepine methanesulfonate Heat a slurry of 7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinyl-carbonyl)-pyrrolo[3,2,1-jk][1,4]benzodiazepine (500 mg, 0.976 mmol) in methanol (2.5 mL) to 64° C. Add a solution of methanesulfonic acid (64 µL, 0.976 mmol) in methanol (1.0 mL) over 5 minutes. Stir the mixture at 64° C. for 15 minutes and then add isopropanol (5.0 mL) over 30 minutes. Allow the resulting slurry to cool to room temperature over 1 hour and then stir at room temperature for 4 hours. Filter the slurry, wash with isopropanol, and dry under reduced pressure at 42° C. to provide the title compound as an orange solid (478 mg, 88.5% (adjusted for 9.9% volatiles in starting material and 1.0% volatiles in product)).

m.p.=282.3° C. (DSC)

Example 3

7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinyl-carbonyl)-pyrrolo[3,2,1-jk][1,4]benzodiazepine ethanolate Heat a slurry of 7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinyl-carbonyl)-pyrrolo[3,2,1-jk][1,4]benzodiazepine (2.0 g, 3.9 mmol) in ethanol (30 mL) to 70° C. Add 5M HCl (0.73 mL) all at once. Stir the mixture at 70° C. for 10 minutes and then add 1N NaOH (3.63 mL) over 3 minutes. Stir the mixture at 70° C. for 2 hours. Allow the resulting slurry to cool to room temperature over 1 hour and then stir at room temperature for 3.5 hours. Filter the slurry, wash with ethanol, and dry under reduced pressure at 42° C. to provide the title compound as an orange solid (1.84 g, 92% (adjusted for 7.5% volatiles in starting material and 7.7% volatiles in product)).

m.p.=179.4° C. (DSC)

Powder X-ray Principal Peaks (Degrees 2 Theta, Intensity): 8.989°, 100%; 9.787°, 48.7%; 12.846°, 20.0%; and 7.444°, 17.5%.

Example 4

7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinyl-carbonyl)-pyrrolo[3,2,1-jk][1,4]benzodiazepine hydrate I Heat a slurry of 7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinyl-carbonyl)-pyrrolo[3,2,1-jk][1,4]benzodiazepine ethanolate (198.5 mg) in water (10 mL) to 80° C. for 2.75 hours. Add 3.11 mL of 1N HCl. When the temperature has returned to 80° C., rapidly add 3.11 mL of 1N NaOH. Allow the temperature to remain at 80° C. for approximately 15 minutes then allow the suspension to cool to room temperature. Collect the solid using vacuum filtration through Whatman #1 paper and allow to dry loosely covered over night. Powder X-ray Principal Peaks (Degrees 2 Theta, Intensity): 12.089°, 100%; 10.485°, 83.6%; 13.227°, 56.0%; and 7.660°, 8.0%.

Example 5

7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinyl-carbonyl)-pyrrolo[3,2,1-jk][1,4]benzodiazepine hydrate II Heat a slurry of 7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinyl-carbonyl)-pyrrolo[3,2,1-jk][1,4]benzodiazepine ethanolate (200.6 mg) in water (25 mL) to 75° C. for 0.5 hours. Add 0.72 mL of 1N HCl and continue to heat for 0.75 hours. Rapidly add 0.72 mL of 1N NaOH. Allow the suspension to cool to room temperature. Collect the solid using vacuum filtration through Whatman #1 paper, rinse with 20 mL deionized water and allow to dry loosely covered for 2 days.

Powder X-ray Principal Peaks (Degrees 2 Theta, Intensity): 6.878°, 100%; 5.732°, 58.7%; 11.550°, 82.8%; 18.426°, 20.7%; and 10.856°, 44.2%.

Example 6

7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinyl-carbonyl)-pyrrolo[3,2,1-jk][1,4]benzodiazepine dihydrate Heat a slurry of 7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinyl-carbonyl)-pyrrolo[3,2,1-jk][1,4]benzodiazepine ethanolate (200.8 mg) in water (25 mL) to 75° C. for 0.67 hours. Add 0.72 mL of 1N HCl and continue to heat for 1.75 hours. Add 0.1N NaOH in 1 mL increments every 5 minutes until 7.2 mL have been added. After the last addition, allow the suspension to remain at 75° C. for 0.67 hours and then allow the suspension to cool to room temperature. Collect the solid using vacuum filtration through Whatman #1 paper, rinse with 20 mL deionized water and allow to dry loosely covered for 2 days. Powder X-ray Principal Peaks (Degrees 2 Theta, Intensity): 5.498°, 100%; 22.149°, 100%; 14.921°, 32.9%; 11.399°, 36.7%; and 11.019°, 20.5%.

Compound I is preferably formulated as a pharmaceutical composition prior to administration to a patient. Useful formulations comprise Compound I or a pharmaceutically acceptable salt or solvate thereof and SBE7-β-CD. The compound SBE7-β-CD is a sulfobutyl ether of β-cyclodextrin described in U.S. Pat. No. 5,134,127. It is sold under the trade name CAPTISOL®. Particular formulations are described in the following Formulation Examples.

A useful pharmaceutical composition may be prepared by dissolving Compound I or a pharmaceutically acceptable salt or solvate thereof (50 mg/mL) in 2-pyrrolidone (SOLU-PHOR®-P). This solution is then diluted with an aqueous solution of SBE7-β-CD (30% by volume) and poloxamer 188 (Lutrol®-F 68) (10% by volume).

Formulation Example 1

Prepare a first solution by adding 30.0 g SBE7-β-CD to 71.25 mL of water and stir or agitate until completely dissolved. Add 10.0 g poloxamer 188 and continue stirring until completely dissolved. Prepare a second solution by adding Compound I ethanolate to 2-pyrrolidone according to the following formula: mL 2-pyrrolidone=(actual Compound I ethanolate wt (mg)/50 mg/mL)×0.5. Add the first solution to the second solution. Filter the resulting solution through a 0.2 µm SUPOR® (hydrophilic polyethersulfone) filter (Pall Corporation) into a dust free container.

A further pharmaceutical composition embodiment is prepared by combining Compound I or a pharmaceutically acceptable salt or solvate thereof in an equimolar amount of a pharmaceutically acceptable acid in water. This mixture is then combined with at least one molar equivalent of SBE7-β-CD as an aqueous solution. Preferred pharmaceutically acceptable acids include HCl, HBr, sulfuric acid and methanesulfonic acid. The use of HCl is especially preferred.

Formulation Example 2

Prepare a first solution by adding 20.0 g SBE7-β-CD to 80.00 mL of water and stir or agitate until completely dissolved. Add this solution to Compound I ethanolate according to the following formula: mL of first solution=(actual Compound I ethanolate wt (mg)/20 mg/mL)−(actual Compound I ethanolate wt (mg)/1200 mg/mL)−(actual Compound I ethanolate wt (mg)×0.00195107 mL of 1N HCl/mg Compound I ethanolate). Add 1N HCl according to the following calculation: mL of 1N HCl to add=(actual Compound I ethanolate wt (mg)×0.00195107 mL of 1N HCl/mg Compound I ethanolate). Stir or bath sonicate until all compound has dissolved.

A preferred pharmaceutical composition embodiment is prepared by adding 1 molar equivalent of Compound I or a pharmaceutically acceptable salt or a solvate thereof to an aqueous solution of at least 1 molar equivalent of SBE7-β-CD at a pH below 5.5 (initial solution pH), optionally in the presence of a pharmaceutically acceptable buffer, and mixing until the Compound I or a pharmaceutically acceptable salt or solvate thereof has dissolved. The pH is then adjusted to between 2.5 and 3.5 with a pharmaceutically acceptable base (final solution pH). This resulting solution formulation may be administered to a patient directly, or the solution may preferably be lyophilized to provide a solid formulation capable of reconstitution with water.

The SBE7-β-CD may be present in the range of 1 molar equivalent up to an amount required to administer no more than 13.4 gm of SBE7-β-CD to a patient in a day. A preferred amount of SBE7-β-CD is from 1.0 to 4.0 molar equivalents, more preferred is from 2.0 to 3.0 molar equivalents, and from 2.5 to 2.7 molar equivalents relative to Compound I is especially preferred.

Although any initial solution pH below 5.5 is acceptable, an initial solution pH below 3.0 is preferred, an initial solution pH in the range of 1.0 to 2.0 is more preferred, and an initial solution pH of between 1.2 and 1.4 is most preferred. The target initial solution pH is achieved by the addition of any pharmaceutically acid capable of adjusting the pH of the solution to a pH less than 5.5. The use of hydrochloric acid is preferred.

The formulation may optionally contain a pharmaceutically acceptable buffer. Pharmaceutically acceptable buffers are those compounds employed by one skilled in the pharmaceutical formulation arts to stabilize the pH of a final solution in a particular pH range. Pharmaceutically acceptable buffers include phosphate buffers as well as citric acid, glycine, and tartaric acid or pharmaceutically acceptable salts thereof. Pharmaceutically acceptable salts of these acids include the sodium and potassium salts. It is preferred that a pharmaceutically acceptable buffer is present in the formulation. Tartaric acid is a preferred pharmaceutically acceptable buffer.

It is important that the Compound I dissolve completely before the pH is adjusted to the final solution pH. Dissolution may be assisted by any mechanical mixing means or by adjusting the temperature of the solution if necessary or desired. Stirring the solution at room temperature is preferred.

The final solution pH is achieved by the addition of any pharmaceutically acceptable base capable of adjusting the pH of the solution to a pH in the range of 2.5 to 3.5. The use of sodium hydroxide is preferred. The final solution pH may be in the range of 2.5 to 3.5, but is preferably in the range of 2.5 to 3.1. A final solution pH in the range of 2.7 to 3.1 is most preferred. Once the final solution pH has been achieved, the solution may be lyophilized if necessary or desired under standard lyophilization conditions to provide a solid pharmaceutical composition suitable for reconstitution with water.

Formulation Example 3

Prepare a solution of 0.15 g tartaric acid and 12 g (5.55 mmol) SBE7-β-CD in 70 mL of water. Add 5 mL of 1.0 N HCl and mix at room temperature. Add 1.1 g (2.15 mmol) Compound I ethanolate and stir at room temperature until dissolved. Add 1N sodium hydroxide to a pH of about 2.9. Add sufficient water to achieve a final volume of 100 mL. Lyophilize this solution to provide an amorphous orange-red solid.

We claim:

1. A method of treating ovarian cancer, non-small cell lung cancer, or colorectal cancer comprising administering to a cancer patient in need of such treatment an effective amount of a chemotherapeutic agent selected from the group consisting of CPT-11, pemetrexed, gemcitabine, etoposide, doxorubicin, cisplatin and carboplatin chemotherapeutic agents in combination with an effective amount of 7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinylcarbonyl)-pyrrolo

[3,2,1-jk][1,4]benzodiazepine or a pharmaceutically acceptable salt or a solvate thereof.

2. An improved method of using CPT-11, pemetrexed, gemcitabine, etoposide, doxorubicin, cisplatin or carboplatin chemotherapeutic agent in the treatment of ovarian cancer, non-small cell lung cancer, or colorectal cancer in a patient in need of such treatment, where the improvement comprises the co-administration of 7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinyl-carbonyl)-pyrrolo[3,2,1-jk][1,4] benzodiazepine or a pharmaceutically acceptable salt or a solvate thereof.

3. A method of claim 1 where the chemotherapeutic agent is cisplatin or carboplatin.

4. A method of treating non-small cell lung cancer comprising administering to a cancer patient in need of such treatment an effective amount of pemetrexed and a cisplatin or carboplatin chemotherapeutic agent in combination with an effective amount of 7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinylcarbonyl)-pyrrolo[3,2,1-jk][1,4] benzodiazepine or a pharmaceutically acceptable salt or a solvate thereof.

5. A method of claim 4 where the chemotherapeutic agent is cisplatin.

* * * * *

UNITED STATES PATENT AND TRADEMARK OFFICE
CERTIFICATE OF CORRECTION

PATENT NO. : 8,318,713 B2  
APPLICATION NO. : 12/664664  
DATED : November 27, 2012  
INVENTOR(S) : Marcio Chedid et al.

Page 1 of 1

It is certified that error appears in the above-identified patent and that said Letters Patent is hereby corrected as shown below:

At First Page Col. 2 (Abstract) Line 5: Delete "-IH-" and insert -- -1H- --,

Signed and Sealed this
Nineteenth Day of February, 2013

Teresa Stanek Rea
*Acting Director of the United States Patent and Trademark Office*